United States Patent [19]

Miura

[11] Patent Number: 5,905,086
[45] Date of Patent: May 18, 1999

[54] REMEDY FOR ANXIETY NEUROSIS

[75] Inventor: Toshiro Miura, Yamaguchi-ken, Japan

[73] Assignee: Chugai Seiyaku Kabushiki Kaisha, Tokyo, Japan; a part interest

[21] Appl. No.: 09/011,668

[22] PCT Filed: Aug. 15, 1996

[86] PCT No.: PCT/JP96/02302

§ 371 Date: Feb. 13, 1998

§ 102(e) Date: Feb. 13, 1998

[87] PCT Pub. No.: WO97/06800

PCT Pub. Date: Feb. 27, 1997

[30] Foreign Application Priority Data

Aug. 15, 1995 [JP] Japan ..................................... 7/208048

[51] Int. Cl.$^6$ .......................... A01N 43/42; A61K 31/44; A61K 41/47
[52] U.S. Cl. .......................... 514/310; 514/307; 514/308; 514/343; 514/355; 514/356; 514/610; 514/611
[58] Field of Search ...................................... 514/310, 307, 514/308, 343, 355, 356, 610, 611

[56] References Cited

U.S. PATENT DOCUMENTS 5,428,039   6/1995   Cohen ...................................... 514/275

OTHER PUBLICATIONS

Endoh et al., *Tohoku J. Exp. Med.*, vol. 130, pp. 199–201, 1980.
Inoue et al., *J. Pharmacol. Exp. Ther.*, vol. 299, No. 3, pp. 793–802, 1984.

*Primary Examiner*—Cecilia J. Tsang
*Assistant Examiner*—Abdel A. Mohamed
*Attorney, Agent, or Firm*—Browdy and Neimark

[57] ABSTRACT

N-(2-Hydroxyethyl)nicotinamide nitrate or its salt prevents or ameliorates anxiety neurosis or panic disorder, or the following anxiety. This compound or its salt has few side effects and exhibits immediate action.

2 Claims, No Drawings

REMEDY FOR ANXIETY NEUROSIS

TECHNICAL FIELD

This invention relates to remedies for anxiety neurosis, in particular, drugs efficacious in treating panic disorder characterized by containing N-(2-hydroxyethyl)nicotinamide nitrate or its salt as the active ingredient.

BACKGROUND ART

Anxiety neurosis means neurosis in a broad sense with anxiety being the predominant symptom. According to DSM-III edited by U.S. Society of Psychiatry in 1980, anxiety neurosis is classified into panic disorder and global anxiety neurosis.

It has been a practice to treat anxiety neurosis including panic disorder with the use of tricyclic antidepressive drugs or benzodiazepine anxiolytic drugs. However, it is pointed out that these drugs suffer from some problems. Namely, the tricyclic antidepressive drugs exert their effects slowly and give rise to cholinolytic side effects. On the other hand, the benzodiazepine anxiolytic drugs induce side effects of hypersedation, break-off phenomenon, etc. and, moreover, produce addiction. That is to say, there has been known no satisfactory remedy for anxiety neurosis.

On the other hand, N-(2-hydroxyethyl)nicotinamide nitrate (generic name: nicorandil) is a known compound which has been marketed as a remedy for angina pectoris and described in, for example, Japanese Patent Publication (Kokai) No. 52-122373. It is known that nicorandil has several effects in addition to the antianginal effect. For example, Japanese Patent Publication (Kokai) No. 53-9323 states that it is efficacious as a remedy for circulatory diseases, while Japanese Patent Publication (Kokai) No. 58-85819 points out its bronchodilating effect. Furthermore, Japanese Patent Publication (Kokai) No. 63-152317 discloses that nicorandil is useful as a remedy for diseases accompanied by cerebral ischemic lesion and Japanese Patent Publication (Kokai) No. 3-101621 indicates that it is useful as a hydroxyl radical scavenger. However, it has not been known that nicorandil and its analogs are useful in the treatment of anxiety neurosis, in particular, panic disorder.

As described above, the tricyclic antidepressive drugs conventionally employed in the treatment of anxiety neurosis, in particular, panic disorder exert their effects slowly and suffer from problems of giving rise to cholinolytic side effects (thirst, constipation, urinary difficulty, etc.) and other serious side effects. On the other hand, it is known that the benzodiazepine anxiolytic drugs induce side effects of hypersedation, break-off phenomenon, drug-addiction, muscle relaxation, etc. Thus, it has been urgently required to develop highly safe drugs by which panic disorder or the following anxiety can be prevented or ameliorated.

DISCLOSURE OF THE INVENTION

Under these circumstances, the present inventors have conducted extensive studies to develop drugs which are efficacious against anxiety neurosis, in particular, panic disorder and exert few side effects. As a result, they have found that N-(2-hydroxyethyl)nicotinamide nitrate or its salt is useful in preventing not only anxiety neurosis but also the following anxiety, thus completing the present invention.

BEST MODE FOR CARRYING OUT THE INVENTION

N-(2-Hydroxyethyl)nicotinamide nitrate (generic name: nicorandil) to be used as the active ingredient in the present invention is a compound which has been marketed as a remedy for angina pectoris. It is possible in the present invention to use marketed nicorandil tablets or injections as such. Alternatively, use may be made therefor of those prepared by, for example, the method described in Japanese Patent Publication (Kokai) No. 52-122373.

Nicorandil to be used as the active ingredient in the present invention may form acid-addition salts together with pharmaceutically acceptable organic or inorganic acids. These salts are also usable in the present invention. Examples of the acid-addition salts include hydrochloride, hydrobromide, phosphate, sulfate, nitrate, oxalate, lactate, tartrate, acetate, salicylate, benzoate, formate, propionate, pivalate, diethylacetate, malonate, succinate, pimelate, fumarate, maleate, malate, sulfamate, phenylpropionate, gluconate, ascorbate, isonicotinate, methanesulfonate, p-toluolsulfonate, citrate, adipate and naphthalenesulfonate.

The term "anxiety neurosis" as used herein means neurosis accompanied by anxiety as the predominant symptom. It can be defined as a disease accompanied mainly by indistinct feelings such as "somehow not being self-possessed", "somehow being frightened" or "failing to keep still" together with physical symptoms, for example, cardiopalmus, palmospasm of fingers, thirst, perspiration, frequent urination, respiratory distress, etc. On the other hand, panic disorder is recognized as a disease falling within the category of anxiety neurosis. It can be defined as a disorder (a disease or syndromes) characterized essentially by repeated panic attacks and accompanied by two or more symptoms such as respiratory distress, palpitation, perspiration, choking feeling, dysaethesia, etc. together with fear of death or insanity. The drugs according to the present invention are useful as remedies for anxiety neurosis, in particular panic disorder. Moreover, they are useful in treating and ameliorating the above-mentioned symptoms caused by these diseases.

It is preferable in the present invention that nicorandil or its salt is processed into an appropriate preparation and then used as a remedy for anxiety neurosis, in particular, panic disorder. Examples of the preparation include tablets, dusts, granules, fine subtilaes, capsules, injections, emulsions, suspensions, suppositories and preparations for percutaneous absorption.

These preparations can be produced in accordance with methods described in Japanese Patent Publication (Kokai) Nos. 57-145659, 58-39618, 61-143316, 62-149630, 62-161727, 62-252722, 62-252723, 63-270624, etc. More particularly speaking, tablets may be produced by mixing nicorandil or its salt with an organic acid (fumaric acid, oxalic acid, salicylic acid, tartaric acid, glutaric acid, etc.) and saturated higher fatty acid(s) being in a solid state at ordinary temperatures (stearic acid, palmitic acid, etc.) or saturated higher alcohol(s) (cetyl alcohol, stearyl aclcohol, etc.), or by mixing nicorandil or its salt with fumaric acid and/or DL-tryptophan.

As the injections, use can be made of those of the non-solution type obtained by mixing nicorandil or its salt with an alkali metal salt of an organic acid (citric acid, fumaric acid, oxalic acid, malonic acid, maleic acid, tartaric acid, etc.). To produce these preparations, it is preferable to further use pharmaceutically acceptable carriers commonly employed in the art such as excipients, disintegrating agents, lubricating agents, binders, perfumes and colorants. Examples of these carriers include lactose, corn starch, mannitol, kaolin, crystalline cellulose, hydroxypropylcellulose, hydroxypropylmethylcellulose, carboxymethylcellulose, carboxymethylcellulose calcium, talc, croscarmellose sodium, anhydrous calcium hydrogenphosphate, calcium carbonate, calcium citrate, calcium stearate and magnesium stearate.

In the present invention, the dose of nicorandil or its salt may be appropriately determined depending on the conditions, figure, constitution, age and sex of the patient, the administration route, the dosage form, etc. In the case of oral administration, the lower limit of the daily dosage generally ranges from 1 to 15 mg, preferably from 5 to 10 mg and still preferably about 7.5 mg, while the upper limit of the daily dosage is generally from 20 to 80 mg, preferably from 25 to 60 mg and still preferably about 30 mg. It may be administered 1 to 4 times in a day. In the case of parenteral administration, the lower limit of the daily dosage is generally ranges from 0.1 to 12 mg, preferably from 0.5 to 6 mg and still preferably from 1 to 2 mg, while the upper limit of the daily dosage is generally from 10 to 50 mg, preferably from 20 to 30 mg and still preferably about 24 mg. It may be administered 1 to 4 times in a day. It is also possible that 12 to 288 mg/day of nicorandil or its salt is intravenously injected continuously.

Such a nicorandil preparation of the present invention may further blended or combined with one or more other antidepressive drugs, anxiolytic drugs or other acceptable drugs.

Examples of antidepressive drugs include imipramine hydrochloride, desipramine hydrochloride, trimipramine hydrochloride, mianserin hydrochloride, amitriptyline hydrochloride, maroptyline hydrochloride, sulpiride, etizolam and carbamazepine. Examples of the anxiolytic drugs include alprazolam, estazolam, oxazolam and diazepam. Examples of the other drugs include sleep promoting drugs such as triazolam, flunitrazepam, phenobarbital and zopiclone; antivertigo drugs such as dimenhydrinate and difenidol hydrochloride; and vasodilator drugs such as dilthiazem hydrochloride, nifedipine hydrochloride, nitroglycerin and isosorbide nitrate.

EXAMPLES

To further illustrate the present invention in greater detail, and not by way of limitation, the following Examples will be given.

Preparation Example 1
Production of nicorandil tablets

| | |
|---|---|
| nicorandil | 10 mg |
| stearic acid | 8 mg |
| mannitol | 65.7 mg |
| corn starch | 15 mg |
| methylcellulose | 0.3 mg |
| magnesium stearate | 1 mg |
| total | 100 mg. |

65.7 g of mannitol, 15 g of corn starch and 0.3 g of methylcellulose SM-400 (manufactured by Shin-Etsu Chemical Co., Ltd.) were well mixed in a mortar and, after adding water, kneaded. The resulting mixture was filtered through a 30-mesh sieve and dried at 45° C. for 3 hours. Then the dried product was dressed by passing through a 30-mesh sieve to thereby give grains. Next, 10 g of nicorandil, 8 g of stearic acid having been filtered through a 30-mesh sieve, 81 g of the grains obtained above and 1 g of magnesium stearate were mixed in a polyethylene-bag and compressed in molds of 7 mm in diameter under pressure of 2,000 kg/cm$^2$ to thereby give tablets each weighing 100 mg.

Preparation Example 2
Production of nicorandil tablets

| | |
|---|---|
| nicorandil | 10 mg |
| stearyl alcohol | 10 mg |
| mannitol | 72.4 mg |
| carboxymethylcellulose calcium | 5 mg |
| hydroxypropylcellulose | 1.6 mg |
| calcium stearate | 1 mg |
| total | 100 mg. |

10 g of stearyl alcohol having been filtered through a 35-mesh sieve, 72.4 g of mannitol, 5 g of carboxymethylcellulose calcium and 1.6 g of hydroxypropylcellulose HPC-L (manufactured by Nippon Soda Co., Ltd.) were well mixed in a mortar and, after adding water, kneaded. The resulting mixture was filtered through a 30-mesh sieve and dried at 40° C. for 5 hours. Then the dried product was dressed by passing through a 30-mesh sieve to thereby give grains. Next, 10 g of nicorandil, 89 g of the grains obtained above and 1 g of calcium stearate were mixed in a polyethylene-bag and compressed in molds of 7 mm in diameter under pressure of 2,000 kg/cm$^2$ to thereby give tablets each weighing 100 mg.

Preparation Example 3
Production of nicorandil tablets

| | |
|---|---|
| nicorandil | 10 mg |
| palmitic acid | 3 mg |
| lactose | 82 mg |
| croscarmellose sodium | 5 mg |
| total | 100 mg. |

10 g of nicorandil, 3 g of palmitic acid having been ground with a jet mill (MICROJET MILL Model FS-4, manufactured by Seishin Kigyo) and having an average diameter of 1 to 3 mm, 82 g of lactose and 5 g of croscarmellose sodium (Ac-Di-Sol™, manufactured by FMC) were mixed in a polyethylene-bag and compressed in molds of 7 mm in diameter under pressure of 2,000 kg/cm$^2$ to thereby give tablets each weighing 100 mg.

Preparation Example 4
Production of nicorandil tablets

| | |
|---|---|
| nicorandil | 10 mg |
| lactose | 76.5 mg |
| corn starch | 10 mg |
| fumaric acid | 3 mg |
| magnesium stearate | 0.5 mg |
| total | 100 mg. |

200 g of nicorandil crystals, 1530 g of lactose, 200 g of corn starch and 60 g of powdered fumaric acid having an average particle size of about 3 mm were supplied into a Shinagawa-mixer and mixed for 20 minutes. Then 10 g of magnesium stearate was further added thereto and the resulting mixture was mixed for 1 minute.

The obtained mixture was then compressed with a single-acting tabletting machine provided with a mortar of 7 mm in diameter and a flat mallet under total pressure of about 1 t to thereby give tablets each weighing 100 mg.

Preparation Example 5
Production of nicorandil capsules

| nicorandil | 10 mg |
|---|---|
| mannitol | 44 mg |
| carboxymethylcellulose calcium | 5 mg |
| salicylic acid | 40 mg |
| calcium stearate | 1 mg |
| total | 100 mg. |

200 g of nicorandil crystals, 880 g of mannitol, 100 g of carboxymethylcellulose calcium, 800 g of salicylic acid crystals and 20 g of calcium stearate were uniformly mixed in a polyethylene-bag and dressed through a 10-mesh sieve to thereby give slag granules. 100 mg of these slag granules were packed in No. 3 capsules.

Preparation Example 6
Production of nicorandil granules

| nicorandil | 50 mg |
|---|---|
| mannitol | 920 mg |
| oxalic acid | 10 mg |
| corn starch | 20 mg |
| total | 1000 mg. |

100 g of nicorandil crystals, 1840 g of mannitol and 20 g of oxalic acid were supplied into a Shinagawa-mixer and mixed for 20 minutes. Next, 400 g of 10% corn starch paste was added thereto and the resulting mixture was kneaded for 10 minutes. The obtained product was granulated in a cylindrical granulator provided with a net of 1.0 mm in diameter. The granules thus obtained were dried in a shelf-drier at 50° C. for 4 hours and then dressed through a 10-mesh sieve.

Preparation Example 7
Production of freeze-dried nicorandil preparation 0.2 g of nicorandil, 0.5 g of sodium citrate and 3 g of mannitol were dissolved in 100 ml of distilled water for injection. The obtained solution was aseptically filtered and pipetted in 1 ml portions into vials. After freeze-drying in a conventional manner, a freeze-dried preparation was obtained.

Example 1
Y.N.: male, age 57, company employee

No remark was given in family history. Past history involved multiple cerebral infarction, anxiety neurosis and hypertension. Since diagnosed as having multiple cerebral infarction in September, 1993, he had a strongly anxious mood and thus took a tranquilizer (etizolam). In November 1993, palpitations became noticeable. Since March, 1994, he had suffered from serious anxious mood and unpleasantness in addition to heartburn, vertigo, anacatesthesia, palpitation, choking feeling, rush of blood to head and fear of death and insanity even though resting quietly. After consultation, a psychiatrist diagnosed him as having anxiety neurosis and gave, in addition to etizolam which had been administered, another tranquilizer (sulpiride), an antivertigo drug (difenidol) and a hypotensive drug (nitrendipine). Inspite of the concentrated drug therapy, his symptoms were not relieved. In response to his complaint of the recurrence of the attack and insomnia, the drug therapy was continued and, moreover, counseling was tried. However, the attack rate rose 4 to 5 times in a month accompanied by presentimental anxiety.

Since May, 1994, the psychiatrist advised him to consult us for detailed examination following breast pain attack. When he came our department for the first time, he had been taking 5 tablets of etizolam together with haloperidol, idebenone and ticlopidine and showed blood pressure of 140/86 (mmHg), cardiac rate of 90 per minute and biochemical blood examination data falling within the normal ranges. At first, it was feared that he might suffer from coronary twitching angina pectoris. Thus a persistent Ca antagonist [dilthiazem hydrochloride: 1 capsule (100 mg)/day] was internally administered and the progress was monitored for 2 months. As a result, neither the anxious mood nor the attack frequency decreased. Thus, 3 tablets (5 mg)/day of a nicorandil 5 mg preparation was further given to him from July, 1994. For a short time after the initiation of the administration of nicorandil, the patient stopped the administration temporarily on his own initiative because of headache seemingly caused by this drug. In September, however, the administration of the nicorandil preparation was started again, since the patient reported that he had been in good condition during the administration period thereof. Attacks did not appear and the anxious mood disappeared. Moreover, the dose of etizolam could be halved for the first time. Since April, 1995, no dilthiazem but 7.5 mg/day of nicorandil had been given to him and the progress had been monitored. In the subsequent 2 months, he had neither any attack nor anxious mood.

Example 2
B.T.: male, age 63, unemployed

Suffering from familial diabetes. Under a diagnosis as diabetes, he had been having diet therapy and remedies for diabetes. He smoked 30 cigarettes a day.

In October and December, 1982, he had a pain in the occipital region and then in the breast continuing for about 1 hour. However, no abnormality was observed neither in cardiac catheter examination nor coronary angiography. Similarly, no abnormality was observed in ergonovine tolerance test or electrocardiogram at the attack in February, 1983.

In the middle of the night in January, 1993, he had a breast pain attack which could be cured 30 minutes thereafter with the use of 2 sublingual tablets of isosorbide nitrate. In this attack, no abnormality was observed either following detailed examination by ultrasound cardiography and Holter's electroradiography. Instead of the following drug therapy with a persistent Ca antagonist and persistent isosorbide nitrate thereafter, he had the attack twice or thrice a month. In May, 1993, he had nitroglycerine-tolerant attack 4 times in a month. Due to frequent breast pain, headache and anacatesthesia accompanying painful stiffness in the neck and shoulders, he was hospitalized in June, 1995. No coronary arterial disease was found in exercise tolerance test, acetylcholine tolerance test and cardiac catheter examination. Although he had an attack in about 2 days during the hospitalization, it was judged that he suffered from no angina pectoris, since no abnormality was observed in ultrasound cardiography and electroradiography at the attack and the breast pain could not be easily relieved by the administration of sublingual tablets of nitrates. Moreover, no abnormality was observed in ultrasound abdominal echography. Based on these results, he was diagnosed as having anxiety neurosis and thus a tranquilizer (etizolam) was administered to him.

In February, 1995, various symptoms accompanying breast pain frequently occurred and could not be relieved by the administration of sublingual tablets of nitroglycerin. Thus, he visited us as an outpatient. During the attack, no abnormality was observed in the electrocardiogram. Also, no abnormality was observed in biochemical blood examination except a somewhat high cholesterol level. After the administration of 2 capsules (100 mg) per day of a persistent Ca antagonist of diltiazem and 15 mg per day of nicorandil, the attacks completely disappeared. The administration of the persistent Ca antagonist was ceased in May, 1995. Although the progress is now under observation with the administration of 15 mg/day of nicorandil alone, no attack has been observed during these 2 months.

Example 3

M.I.: male, age 44, company employee

No remark was given in family history. Suffering from hypertension and being under treatment with a hypotensive drug (prazosin). He smoked 30 cigarettes a day.

Since March, 1994, he had vertigo followed by palpitation, choking feel, hyperpnea, etc. without no specific cause. These symptoms continued for about 1 to 2 hours followed by spontaneous amelioration.

When he visited us in April, 1995, he showed blood pressure of 130/80 (mmHg), cardiac rate of 70 per minute and biochemical blood examination data falling within the normal ranges. No abnormality in the cardiopulmonary function was observed in thoracic radiography and electrocardiography. In the electrocardiogram, no ischemic change but sinus tachycardia alone was observed. Thus, it was judged that he suffered from no angina pectoris. Since he showed normal thyroid function, he was diagnosed as having anxiety neurosis with panic disorder. After administering 7.5 mg/day of nicorandil, the anxious mood disappeared and no attack was observed during the monitoring period for 2 months thereafter. No combined drug therapy was employed.

Example 4

S.I.: male, age 54, company employee

No remark was given in family history. Suffering from amyloidosis of skin and hypertension and being under treatment with a hypotensive drug (enalapril). He was posted to Osaka away from his family. When washing his face in March, 1995, he had thoracic compression followed by cold flush, hyperpnea, choking feeling and anxious mood which continued for 30 minutes. Subsequently, he had similar attacks 5 times in a month. Thus, he took time off from work, came back home and visited us.

When he visited us in May, 1995, he showed blood pressure of 206/110 (mmHg), cardiac rate of 70 per minute and no abnormality in biochemical blood examination. Also, no abnormality was observed in thoracic radiography, electrocardiography and ultrasound cardiography. Thus, it was judged that he suffered from not angina pectoris but anxiety neurosis with panic attack.

During 2 months from the initiation of the administration of 15 mg/day of nicorandil, he had no attack and the anxious mood disappeared, which enabled him to go back to work. Now, he is taking no drug but 1 tablet/day of a hypotensive drug (enalapril) for treating hypertension.

Example 5

T.I.: male, age 43, teacher

Although no remark was given either on family history or past history, he had a phlegmatic temperament. When studying in United States in 1994, he had breast pain, thoracic unpleasantness, cold flush, insomnia, anxious mood, palpitation, shortness of breath, frequent respiration and fear of death. Since no abnormality was observed in his electrocardiogram, exercise tolerance data and ultrasound cardiogram, a cardiac disease specialist diagnosed him as having anxiety neurosis. Although he had drug therapy with etizolam, the symptoms did not disappear. After coming back to Japan in December, 1994, he had the same attack once or twice a month with a strong anxious mood. When he hospitalized as an emergency outpatient in January, April and June in 1995, no ischemic change but sinus tachycardia alone was observed in electrocardiography. Thus, it was judged that he suffered from no cardiac disease.

When he visited us in June, 1995, he showed blood pressure of 130/80 (mmHg), cardiac rate of 95 per minute and no abnormality in biochemical blood examination and thyroid function. Although he showed sinus tachycardia (120–140/min) in detailed Holter's electroradiography at the attack, no ischemic change was observed. Thus, we diagnosed him as having anxiety neurosis with panic attack, similar to the former cases. It had been recommended him to take a tranquilizer (etizolam) and an anxiolytic drug (alprazolam). However, he scarcely took etizolam, since it made him listless. Since aplrazolam made him sleepy, on the other hand, he took it exclusively at the bedtime. Thus the administration of etizolam was stopped and nicorandil (7.5 mg/day) was administered together with alprazolam. He had no attack thereafter and the anxious mood disappeared, which enabled him to go back to work.

INDUSTRIAL APPLICABILITY

It has been a practice to treat anxiety disorders typified by panic disorder with the use of drugs such as tricyclic antidepressive drugs and benzodiazepine anxiolytic drugs. However, these drugs exert their effects only slowly and, moreover, suffer from some problems in safety, for example, a fear of serious side effects and drug-addiction. In contrast thereto, it is believed that the nicorandil remedies for anxiety neurosis in accordance with the present invention are ideal ones capable of exhibiting immediate actions with few safety problems.

I claim:

1. A method for treating anxiety neurosis comprising administering an effective amount of N-(2-hydroxyethyl) nicotinamide nitrate or its salt as an active ingredient.

2. A method for treating panic disorder comprising administering an effective amount of N-(2-hydroxyethyl) nicotinamide nitrate or its salt as an active ingredient.

* * * * *